(12) United States Patent
Drysdale

(10) Patent No.: US 8,962,879 B2
(45) Date of Patent: Feb. 24, 2015

(54) PERFLUOROPOLYVINYL MODIFIED ARYL INTERMEDIATES/MONOMERS

(71) Applicant: E I Du Pont De Nemours and Company, Willmington, DE (US)

(72) Inventor: Neville Everton Drysdale, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 14/068,603

(22) Filed: Oct. 31, 2013

(65) Prior Publication Data

US 2014/0135524 A1 May 15, 2014

Related U.S. Application Data

(60) Provisional application No. 61/726,267, filed on Nov. 14, 2012.

(51) Int. Cl.
 *C07C 69/62* (2006.01)
 *C07C 69/653* (2006.01)

(52) U.S. Cl.
 CPC .................................. *C07C 69/653* (2013.01)
 USPC ........................................................ 560/221

(58) Field of Classification Search
 None
 See application file for complete search history.

(56) References Cited

U.S. PATENT DOCUMENTS

| | | | |
|---|---|---|---|
| 4,460,791 A | 7/1984 | Cooke | |
| 4,577,036 A | 3/1986 | Falk | |
| 4,876,018 A | 10/1989 | Karydas | |
| 5,198,570 A | 3/1993 | Feiring | |
| 5,643,495 A | 7/1997 | Bartmann et al. | |
| 5,646,222 A | 7/1997 | Maekawa et al. | |
| 7,531,700 B2 | 5/2009 | Petrov | |
| 2006/0006364 A1 | 1/2006 | Shundo et al. | |
| 2007/0134440 A1 | 6/2007 | Kato | |
| 2011/0001088 A1 | 1/2011 | Ootsuki et al. | |
| 2012/0277460 A1 | 11/2012 | Percec et al. | |

FOREIGN PATENT DOCUMENTS

| | | | |
|---|---|---|---|
| DE | 3828063 A1 | 2/1990 | |
| DE | 3828064 A1 * | 3/1990 | |
| DE | 4015681 A1 | 11/1991 | |
| DE | 4015681 C2 | 11/1991 | |
| EP | 0295813 A2 | 12/1988 | |
| EP | 0355025 A2 | 8/1989 | |
| EP | 0355025 A3 | 8/1989 | |
| EP | 0391390 A1 | 10/1990 | |
| EP | 0391390 B1 | 10/1990 | |
| EP | 0610861 A1 | 8/1994 | |
| EP | 0638629 A2 | 2/1995 | |
| EP | 0638629 A3 | 2/1995 | |
| EP | 0638629 B1 | 2/1995 | |
| EP | 1036790 A1 | 9/2000 | |
| EP | 1411104 A1 | 4/2004 | |
| EP | 1411104 B1 | 5/2007 | |
| GB | 1376315 A | 12/1974 | |
| GB | 1404351 A | 8/1975 | |
| GB | 2245587 A | 1/1992 | |
| JP | 04159272 | 6/1992 | |
| JP | 1994172266 A | 6/1994 | |
| JP | 1997255608 A | 9/1997 | |
| JP | 2961164 B2 | 10/1999 | |
| JP | 2006117564 A | 5/2006 | |
| JP | 2006137856 A | 6/2006 | |
| JP | 2011148761 A | 8/2011 | |
| WO | 2007/149449 A2 | 12/2007 | |
| WO | 2007/149449 A3 | 12/2007 | |

OTHER PUBLICATIONS

U.S. Appl. No. 14/068,535, filed Oct. 31, 2013, Drysdale.
U.S. Appl. No. 14/068,784, filed Oct. 31, 2013, Drysdale.
U.S. Appl. No. 14/068,930, filed Oct. 31, 2013, Drysdale.
Search Report and Written Opinion, PCT/2013/069020 Dated Jan. 20, 2014.
Search Report and Written Opinion, PCT/2013/069029 Dated Jan. 7, 2014.
Search Report and Written Opinion, PCT/2013/069031 Dated Jan. 14, 2014.
Furin, G. et al. "Reaction of 1,1,2-trifluoro-2-hexaflouro-2'-(heptafluoropropoxy-propoxyethylene with amines or alcohols", Journal of Fluorine Chemistry, 106, Dated Mar. 15, 2000, pp. 13-24, XP002718135.

(Continued)

*Primary Examiner* — Brandon Fetterolf
*Assistant Examiner* — Ana Z Muresan

(57) ABSTRACT

A compound of formula (I)

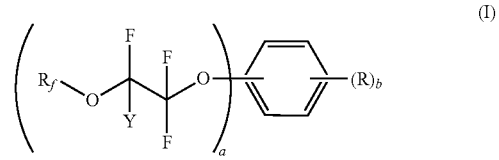

wherein
 $R_f$ is —$CF_3$, —$C_2F_5$, —$CF_2CFXCF_3$;
 X to —F, or —$OC_3F_7$;
 Y is —H, —Cl, or —Br;
 R is —O—C(O)—$R^1$, —$(CH_2)_n$O—C(O)—$R^1$, —$(OCH_2CH_2)_m$OC(O)—$R^1$; —$(CH_2)_n(OCH_2CH_2)_m$O—$R^1$;
 n is 1 to 10;
 m is 1 to 10;
 $R^1$ is —$C(R^3)$=$CH_2$;
 $R^3$ is H or $CH_3$;
 a is 1 to 5; and
 b is 1 to 5.

13 Claims, No Drawings

(56) References Cited

OTHER PUBLICATIONS

Dlouha, Ivine, Reactivity Study of 1,1,2,4,4,5,7,7,8,8,9,9,9-tridecafluoro-5-trifluoromethyl-3,6-dioxanon-1-ene in nucleophilic reactions: fluorination properties of secondary amine adducts, Journal Of Fluorine Chemistry, 117, Dated May 20, 2002, pp. 149-159.

Non-Final Office Action Dated Sep. 30, 2014.

Search Report and Written Opinion, PCT/2014/062643 Dated Dec. 12, 2014.

* cited by examiner

PERFLUOROPOLYVINYL MODIFIED ARYL INTERMEDIATES/MONOMERS

FIELD OF THE INVENTION

The present invention comprises aryl compounds having partially fluorinated pendent groups and (meth)acrylate dependent groups, useful for free radical polymerization. The resulting polymers are useful for producing various water and oil repellents, soil resists, and surfactants.

BACKGROUND OF THE INVENTION

Water and oil repellents, soil resists, and surfactants compounds generally are prepared from linear perfluorinated alcohols. These alcohols are expensive and are prepared through several step syntheses. These alcohols are either then reacted to make final products or further synthesized into intermediates prior to making final products. New starting materials are needed that do not utilize linear uninterrupted perfluorinated alcohols, which are in short supply.

U.S. Pat. No. 7,531,700 teaches fluorinated solvents having benzene rings with a) perfluorinated pendent alkyl groups, b) alkyl, alkoxy, or oxyalkyl groups and c) optionally halogen pendent groups useful for the manufacture of organic electronic devices. These solvents are non-reactive.

Patent Application WO 2007/149449 teaches fluoroalkoxystyrenes prepared by contacting a fluorinated olefin with a solution of hydroxystyrene. These fluoroalkoxystyrenes are useful in resins, elastomers, polymers, or coatings.

Compounds other than linear uninterrupted perfluorinated alcohols are needed which can be used as starting monomers to produce polymers for water and oil repellents and soil resists. The present invention meets this need.

SUMMARY OF THE INVENTION

A compound of formula (I)

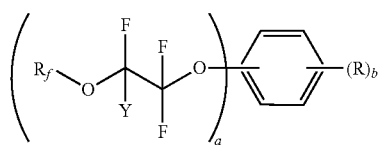

wherein
$R_f$ is —$CF_3$, —$C_2F_5$, —$CF_2CFXCF_3$;
X to —F, or —$OC_3F_7$;
Y is —H, —Cl, or —Br;
R is —O—C(O)—$R^1$, —$(CH_2)_nO$—C(O)—$R^1$, —$(OCH_2CH_2)_mOC(O)$—$R^1$; —$(CH_2)_n(OCH_2CH_2)_mO$—$R^1$;
n is 1 to 10;
m is 1 to 10;
$R^1$ is —C($R^3$)=$CH_2$;
$R^3$ is H or $CH_3$;
a is 1 to 5; and
b is 1 to 5.

DETAILED DESCRIPTION

Herein trademarks are shown in upper case.
The term "(meth)acrylate" is used herein defined to mean both "acrylate" and "methacrylate".

The present invention relates to a compound of formula (I)

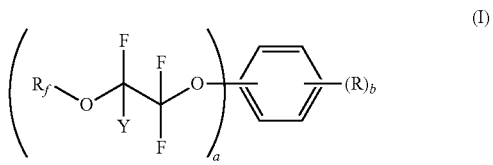

wherein
$R_f$ is —$CF_3$, —$C_2F_5$, —$CF_2CFXCF_3$;
X to —F, or —$OC_3F_7$;
Y is —H, —Cl, or —Br;
R is —O—C(O)—$R^1$, —$(CH_2)_nO$—C(O)—$R^1$, —$(OCH_2CH_2)_mOC(O)$—$R^1$; —$(CH_2)_n(OCH_2CH_2)_mO$—$R^1$;
n is 1 to 10;
m is 1 to 10;
$R^1$ is —C($R^3$)=$CH_2$;
$R^3$ is H or $CH_3$;
a is 1 to 5; and
b is 1 to 5.

Compounds of the present invention include pendent groups ($R_f$—O—CFY—$CF_2O$—)$_a$ and (R)$_b$ and wherein a is 1, 2, 3, 4, or 5, and b is 1, 2, 3, 4 or 5. Compounds of the present invention may 1, 2, 3, 4, or 5 pendent groups of $R_f$—O—CFY—$CF_2O$—, 1, 2, 3, 4, or 5 pendent groups of —R, and mixtures thereof, provided that the total number of pendent groups is less than or equal to 6. The $R_f$—O—CFY—$CF_2O$— and —R groups may be ortho, para, or meta on the benzene ring or combinations thereof.

Preferred compounds of Formula (I) include those wherein $R_f$ is —$CF_3$, or —$C_2F_5$; Y is H; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, a, and b are defined as above; n is 1, 2, 3, 4, 5, or 6; and m is 1, 2, 3, 4, 5, or 6.

Also preferred are compounds of Formula (I) wherein $R_f$ is —$CF_3$, or —$C_2F_5$; Y is H; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, a, and b are defined as above; n is 1, 2, or 3; and m is 1, 2, or 3.

Additional preferred compounds of Formula (I) include those wherein $R_f$ is —$CF_3$, or —$C_2F_5$; Y is H; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, m, and n are defined as above; a is 1, 2, or 3; and b is 1, 2, or 3. Also preferred are compounds of Formula (I) wherein $R_f$ is —$CF_3$, or —$C_2F_5$; Y is H; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, m, and n are defined as above; a is 1, or 2; and b is 1, or 2.

Additional preferred compounds of Formula (I) include those wherein $R_f$ is —$CF_3$, or —$C_2F_5$; Y is Cl or Br; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, a, and b are defined as above; n is 1, 2, 3, 4, 5, or 6; and m is 1, 2, 3, 4, 5, or 6. Also preferred are compounds of Formula (I) wherein $R_f$ is —$CF_3$, or —$C_2F_5$; Y is Cl or Br; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, a, and b are defined as above; n is 1, 2, or 3; and m is 1, 2, or 3.

Preferred compounds of Formula (I) also include those wherein $R_f$ is —$CF_2CFXCF_3$; X is F; Y is H, Cl or Br; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, a, and b are defined as above; n is 1, 2, 3, 4, 5, or 6; and m is 1, 2, 3, 4, 5, or 6. Also preferred are compounds of Formula (I) wherein $R_f$ is —$CF_2CFXCF_3$; X is F; Y is H, Cl or Br; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, a, and b are defined as above; n is 1, 2, or 3; and m is 1, 2, or 3.

Additional preferred compounds of Formula (I) include those wherein $R_f$ is —$CF_2CFXCF_3$; X is —$OC_3F_7$; Y is H, Cl or Br; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, a, and b are defined as above; m is 1, 2, 3, 4, 5, or 6; and n is 1, 2, 3, 4, 5, or 6. Also preferred are compounds of Formula (I) wherein $R_f$ is —$CF_2CFXCF_3$; X is —$OC_3F_7$; Y is H, Cl or Br; R is —O—C(O)—$R^1$, —$(CH_2)_nO$—C(O)—$R^1$, —$(OCH_2CH_2)_mOC(O)$—$R^1$, or —$(CH_2)_n(OCH_2CH_2)_mO$—$R^1$; $R^1$, $R^3$, a, and b are defined as above; n is 1, 2, or 3; and b is 1, 2, or 3.

Compounds of Formula (I) can be produced in various ways. Examples of compounds of Formula (I) include, but are not limited to,

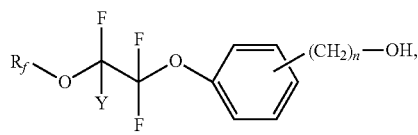

(II)

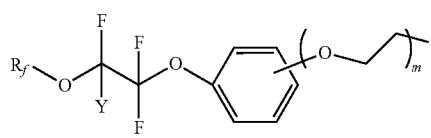

(III)

and

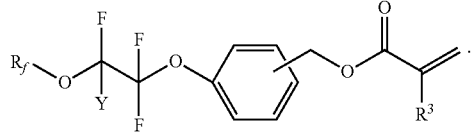

(IV)

In the present invention, (meth)acrylate containing compounds of Formula (I) wherein $R_f$ is —$CF_3$, —$C_2F_5$, —$CF_2CFXCF_3$; X is —F, or —$OC_3F_7$; and Y is —H, —Cl, or —Br; and R is —O—C(O)—$R^1$, —$(CH_2)_nO$—C(O)—$R^1$, —$(OCH_2CH_2)_mOC(O)$—$R^1$; —$(CH_2)_n(OCH_2CH_2)_mO$—$R^1$; n is 1 to 10; m is 1 to 10; $R^1$ is —$C(R^3)$=$CH_2$; $R^3$ is H or $CH_3$; a is 1 to 5; and b is 1 to 5 can be prepared by contacting compounds of Formula (I) wherein $R_f$ is —$CF_3$, —$C_2F_5$, —$CF_2CFXCF_3$; X is —F, or —$OC_3F_7$; and Y is —H, —Cl, or —Br and R is —$(CH_2)_nOH$, —$(OCH_2CH_2)_mOH$, —$(CH_2)_n(OCH_2CH_2)_mOH$ with methyl (meth)acrylate and a catalyst, such as titanium(IV) butoxide.

Compounds of Formula (I) wherein $R_f$ is —$CF_3$, —$CF_3$, —$C_2F_5$, —$CF_2CFXCF_3$; X is —F, or —$OC_3F_7$; and Y is —H, —Cl, or —Br and R is —$(CH_2)_nOH$, —$(OCH_2CH_2)_mOH$, —$(CH_2)_n(OCH_2CH_2)_mOH$ can be prepared by can be prepared by contacting functionalized aryl rings of Formula (V)

(V)

wherein a is 1 to 5 and b is 1 to 5;

with one or more perfluorovinyl ethers of formula (VI)

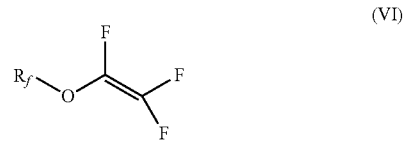

(VI)

wherein $R_f$ is —$CF_3$, —$C_2F_5$, —$CF_2CFXCF_3$; X is —F, or —$OC_3F_7$; and Y is —H, —Cl, or —Br.

For compounds of Formula (VI), when $R_f$ is —$CF_3$, the compound is perfluoromethylvinyl ether of Formula (VII)

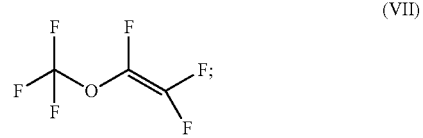

(VII)

when $R_f$ is —$C_2F_5$, the compound is a perfluorovinyl ethyl ether of Formula (VIII)

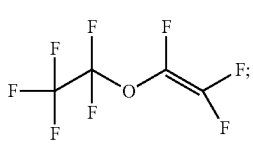

(VIII)

when $R_f$ is —$CF_2CFXCF_3$ and X is —F, the compound is a perfluoropropylvinyl ether of Formula (IX)

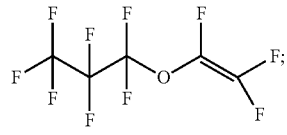

(IX)

and when $R_f$ is —$CF_2CFXCF_3$ and X is —$OC_3F_7$, the compound is a perfluoropropylvinyl ether of Formula (X)

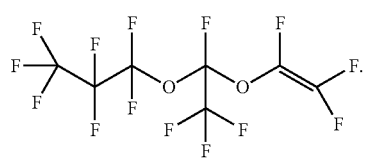

(X)

The reaction of the aryl compounds of Formula (XIII) with perfluorovinyl ethers of Formula (XIV) can be completed in a solvent and a base. Examples of such bases include, but are not limited to, potassium carbonate, sodium carbonate, and potassium bicarbonate. Examples of suitable solvents include, but are not limited to, tetrahydrofuran, carbon tetrachloride, and carbon tetrabromide. In Formula (I), when tetrahydrofuran is the solvent, then Y is H. In Formula (I), when carbon tetrachloride is the solvent, then Y is Cl. In Formula (I), when carbon tetrabromide is the solvent, then Y is Br. The reaction temperature can between room temperature and the solvent reflux temperature.

Compounds of the present invention and above defined embodiments are useful, for example, as starting monomers and intermediates for the preparation of polyacrylate copolymers used for oil is and water repellency as well as stain resistance to fibrous substrates.

EXAMPLES

Materials

Perfluorovinyl ethers 1,1,1,2,2,3,3-heptafluoro-3-((1,2,2-trifluorovinyl)oxy)propane and 1,1,1,2,2,3,3-heptafluoro-3-(1,1,1,2,3,3-hexafluoro-3-(1,2,2trifluorovinyloxy)propan-2-yloxy)propane are commercially available from E. I. du Pont de Nemours and Company, Wilmington, Del. All other reactants, unless otherwise specified, are available from Sigma-Aldrich, St. Louis, Mo.

Example 1

4-(1,1,2-trifluoro-2-(1,1,2,3,3,3-hexafluoro-2-(perfluoropropoxy)propoxy)ethoxy)benzyl methacrylate

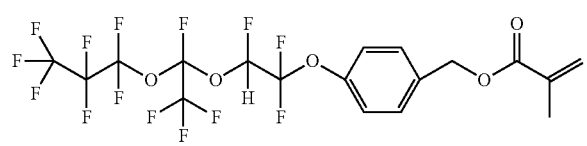 [SMILES: C=C(C)C(=O)OCc1ccc(OC(F)(F)C(F)OC(F)(OC(F)(F)C(F)(F)C(F)(F)F)C(F)(F)F)cc1]

In a dry box, tetrahydrofuan (50 mL) and 4-(hydroxymethyl)phenol (0.62 g, 0.005 mol) were added to a round bottom flask equipped with a stirrer. Potassium carbonate (0.345 g, 0.0025 mol) was then added to the flask. 1,1,2,2,3,3-Heptafluoro-3-(1,1,1,2,3,3-hexafluoro-3-(1,2,2trifluorovinyloxy)propan-2-yloxy)propane (3.24 g, 0.0075 mol) was then added via the addition funnel and the reaction was placed in an oil bath and heated to a gentle reflux over 2 days. The content was analyzed by proton NMR and shown to be (4-(1,1,2-trifluoro-2-(1,1,2,3,3,3-hexafluoro-2-(perfluoropropoxy)propoxy)ethoxy)phenyl)methanol.

In the dry box, the (4-(1,1,2-trifluoro-2-(1,1,2,3,3,3-hexafluoro-2-(perfluoropropoxy)propoxy)ethoxy)phenyl)methanol (36.5 g, 0.656 mol) and methyl methacrylate (40.0 g, 0.40 mol) were added to a round bottom flask equipped with a stirrer. Titanium(iv) n-butoxide (0.50 mL) was then added to the round bottom flask. The reaction was placed in an oil bath and heated to reflux over about 3 hours. Then the reaction product was distilled to remove excess methyl methacrylate. The content was analyzed by proton NMR and shown to be 4-(1,1,2-trifluoro-2-(1,1,2,3,3,3-hexafluoro-2-(perfluoropropoxy)propoxy)ethoxy)benzyl methacrylate.

Example 2

2-(1,1,2-trifluoro-2-(perfluoropropoxy)ethoxy)phenoxy)ethyl methacrylate

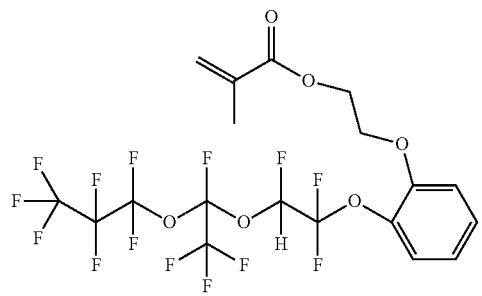 [SMILES: C=C(C)C(=O)OCCOc1ccccc1OC(F)(F)C(F)OC(F)(OC(F)(F)C(F)(F)C(F)(F)F)C(F)(F)F]

In a dry box, tetrahydrofuan (50 mL) and 2-(hydroxyethoxy)phenol (0.77 g, 0.005 mol) were added to a round bottom flask equipped with a stirrer. Potassium carbonate (0.345 g, 0.0025 mol) was then added to the flask. 1,1,1,2,2,3,3-Heptafluoro-3-(1,1,1,2,3,3-hexafluoro-3-(1,2,2trifluorovinyloxy)propan-2-yloxy)propane (3.24 g, 0.0075 mol) was then added via the addition funnel and the reaction was placed in an oil bath and heated to a gentle reflux overnight. The content was analyzed by proton NMR and shown to be 2-(2-(1,1,2-trifluoro-2-(1,1,2,3,3,3-hexafluoro-2-(perfluoropropoxy)propoxy)ethoxy)phenoxy)ethanol.

In the dry box, the 2-(2-(1,1,2-trifluoro-2-(1,1,2,3,3,3-hexafluoro-2-(perfluoropropoxy)propoxy)ethoxy)phenoxy)ethanol (35.0 g, 0.083 mol) and methyl methacrylate (64.0 g, 0.640 mol) were added to around bottom flask equipped with a stirrer. Titanium(iv) n-butoxide (0.50 mL) was then added to the round bottom flask. The reaction was placed in an oil bath and heated to reflux over about 3 hours. Then the reaction product was distilled to remove excess methyl methacrylate. The content was analyzed by proton NMR to be 2-(2-(1,1,2-trifluoro-2-(1,1,2,3,3,-hexafluoro-2-(perfluoropropoxy)ethoxy)phenoxy)ethyl methacrylate. The excess methacrylate was removed under reduced pressure and vacuum distillation of the resulting material gave 9.30 g of the pure material, bp 107-110 at 0.85 torr.

What is claimed is:
1. A compound of formula (I)

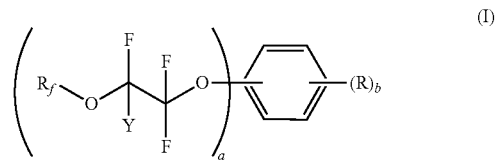

wherein
$R_f$ is —$CF_3$, —$C_2F_5$, —$CF_2CFXCF_3$;
X to —F, or —$OC_3F_7$;
Y is —H, —Cl, or —Br;
R is —O—C(O)—$R^1$, —$(CH_2)_n$O—C(O)—$R^1$, —$(OCH_2CH_2)_m$OC(O)—$R^1$; —$(CH_2)_n(OCH_2CH_2)_m$O—$R^1$;

n is 1 to 10;
m is 1 to 10;
$R^1$ is —C($R^3$)=CH$_2$;
$R^3$ is H or CH$_3$;
a is 1 to 5; and
b is 1 to 5.

2. A compound of claim 1, wherein $R_f$ is —CF$_3$.
3. A compound of claim 1, wherein $R_f$ is —C$_2$F$_5$.
4. A compound of claim 1, wherein $R_f$ is —CF$_2$CFXCF$_3$ and X is —F.
5. A compound of claim 1, wherein $R_f$ is —CF$_2$CFXCF$_3$ and X is —OC$_3$F$_7$.
6. A compound of claim 1, wherein R is —O—C(O)—$R^1$.
7. A compound of claim 1, wherein R is —(CH$_2$)$_n$O—C(O)—$R^1$.
8. A compound of claim 1, wherein R is —(OCH$_2$CH$_2$)$_m$OC(O)—$R^1$.
9. A compound of claim 1, wherein Y is —H.
10. A compound of claim 1, wherein Y is —Cl.
11. A compound of claim 1, wherein Y is —Br.
12. A compound of claim 1, wherein $R^3$ is —H.
13. A compound of claim 1, wherein $R^3$ is —CH$_3$.

\* \* \* \* \*